United States Patent [19]

Hagen

[11] Patent Number: 4,498,465
[45] Date of Patent: Feb. 12, 1985

[54] ERECTILE PROSTHESIS

[75] Inventor: Glenn E. Hagen, New Orleans, La.

[73] Assignee: Hagen Medical Equipment Corporation, Carson City, Nev.

[21] Appl. No.: 385,446

[22] Filed: Jun. 7, 1982

[51] Int. Cl.³ ............................................... A61F 5/42
[52] U.S. Cl. ............................................... 128/79; 3/1
[58] Field of Search ................................... 128/79; 3/1

[56] References Cited

U.S. PATENT DOCUMENTS

| 764,801 | 7/1904 | Emerson | 128/79 |
| 3,446,206 | 5/1969 | De Lano | 128/79 |
| 3,759,253 | 9/1973 | Cray | 128/79 |

OTHER PUBLICATIONS

F. Coiffman, "An External Prosthesis for Treatment of Sexual Impotence", *Transactions of Fifth International Congress of Plastic and Reconstructive Surgery*, 1970, pp. 1273-1277.

Primary Examiner—Stephen C. Pellegrino

[57] ABSTRACT

The present invention is an apparatus and surgical procedure method, which together comprise a medical prosthesis to mimic the erectile response of the adult human male.

3 Claims, 17 Drawing Figures

4a

4a

4b

ERECTILE PROSTHESIS

TECHNICAL FIELD

The present invention relates to surgical procedures and prostheses for the treatment of impotence of the adult human male.

BACKGROUND ART

Urologists have long been aware of the inability of the current state of the art in medicine to surgically manage the failure of erection in men. Scardino first recognized the needs of these patients and realistically endeavored to reestablish a functionally erect penis by using a centrally placed acrylic rod beneath Buck's fascia on the dorsum of the penis. The result was a flaccid penis reenforced against buckling of the shaft, which provided for adequate vaginal penetration. Other pioneers, such as Goodwin and Scott, Lash, Zimmerman and Loeffler, and Pearman were among the early pioneers in the surgical rigid rod prosthesis. These early devices were not very satisfactory because they resulted in a semipermanent erection.

These centrally placed semirigid rod prostheses were soon replaced by paired semirigid rods implanted within the corpora cavernosa of the penis. Beheri, Small, Carrion and Gordon, and, more recently, Finney, have applied this surgical technique in an effort to provide a more nearly normal erectile state suitable for vaginal penetration and satisfactory intercourse. In this regard, these prosthetic devices have been satisfactory. They suffer, however, from a shortcoming common to all prior art in this area, i.e., they result in a semipermanent erection. Further, insertion of the rods is surgery, which has its own attendant risks. Finally, surgical implantation of these rods in the penis often removes the possibility of normal erection.

The hydraulically inflatable penile prosthesis, developed by Scott, Bradley and Timm, was first introduced in 1973 for surgical correction of organic impotence. This device comprises four parts: An inflate-deflate pump, a storage reservoir and paired inflatable cylinders composed of medical-grade silicone elastomer. This prior art requires major surgery for implantation of the removable cylinders and removes the possibility of normal erection. Unlike rods, these hydraulically inflatable prostheses can malfunction mechanically. Nonetheless, they were a great improvement over the use of paired semirigid rods. Unfortunately, the prior art techniques are medically hazardous.

Dr. William L. Furlow, in his article, "Inflatable Penile Prosthesis: Mayo Clinic Experience with 175 Patients", *Urology*, Volume XIII, Number 2, February, 1979, reported that, of 175 patients treated for impotence with an inflatable penile prosthesis, 37 had mechanical complications, such as buckling of the cylinder, rupture of the cylinder, loss of fluid, etc.; while 13 had pathological complications, such as infection or wound erosion. Kramer et al., in the article "Complications of Small-Carrion Penile Prosthesis", *Urology*, Volume XIII, Number 1, January, 1979, discusses the complications that occur from use of the Small-Carrion penile prosthesis, which is one of the most popular and widely used prosthesis known to the prior art. Seventy-six patients with impotence underwent insertion of the prosthesis. Twenty patients experienced postoperative complications. Seven of these twenty lost one or both parts of the prosthesis either by spontaneous extrusion or surgical removal. Two of the seven patients presented obstructive symptoms of the urinary tract and purulent urethral drainage. In both patients, the prosthesis eroded through the corpus cavernosum into the urethra and was spontaneously extruded. Among the problems noted as most frequent by Dr. Kramer included wound infection, erosion of the corpus cavernosum, migration of the prosthesis into the urethra, and problems with concealment.

All prior art known to the present inventor, therefore, requires relatively nontrivial surgery that can result in complications. The prostheses are either mechanically complicated and subject to failure or result in a permanent or semipermanent erection. In all cases, medical authorities agree that psychological trauma associated with use of the prosthesis is an important aspect of treatment of impotence. Finally, surgical procedures to correct impotence are not normally used on subjects who can have any regular erection, due to the fact that the surgical procedure generally prevents the possibility of a normal erection.

DISCLOSURE OF THE INVENTION

The present invention is a prosthesis comprising an apparatus used to erect the adult male penis and an out-patient surgery procedure used to adapt the penis for functional engagement with the apparatus.

The surgical procedure of the present invention involves the formation of a pocket in the foreskin or forward portion of the penis that is capable of receiving the engaging head of the prosthesis apparatus.

The prosthesis apparatus is a relatively rigid shaft mounted on a base or pad that is contoured to compressively engage the layer of fatty tissue at the base of the penis, i.e., the pubic region. The rigid shaft of the present invention has a removable bulbous head adapted to engage the skin pocket created by the surgery mentioned above.

The present invention is an improvement over the prior art because the surgery used to create a skin pocket capable of receiving the prosthesis apparatus in no way interferes with normal erection or ejaculation. Thus, the present invention can be used with occasionally impotent patients because it permits normal erection, orgasm and ejaculation.

The present invention is external and if the patient is uncircumcised, the surgery required to create the engaging pocket is trivial.

The present invention is removable and need only be used by the patient when the patient desires intercourse. In this regard, it is a significant improvement over rigid implants.

Even for circumcised patients, the surgery required to adapt the penis to the apparatus of the present invention is an out-patient operation that can be performed under local anesthetic. Since the surgery is simple and minor, the present invention does not result in many of the complications found in the prior art.

Perhaps one of the most important advantages offered by the present invention is that it does not preclude using prior art prostheses, should they later be desired. This minimizes the severe psychological trauma frequently associated with prior art prosthesis. The present invention, being external and requiring only minor surgery, does not prevent a patient from later undergoing the radical surgery required to install a hydraulic inflatable prosthesis, a semirigid rod prosthesis or the like.

BEST MODE FOR CARRYING OUT THE INVENTION

Figure 1:
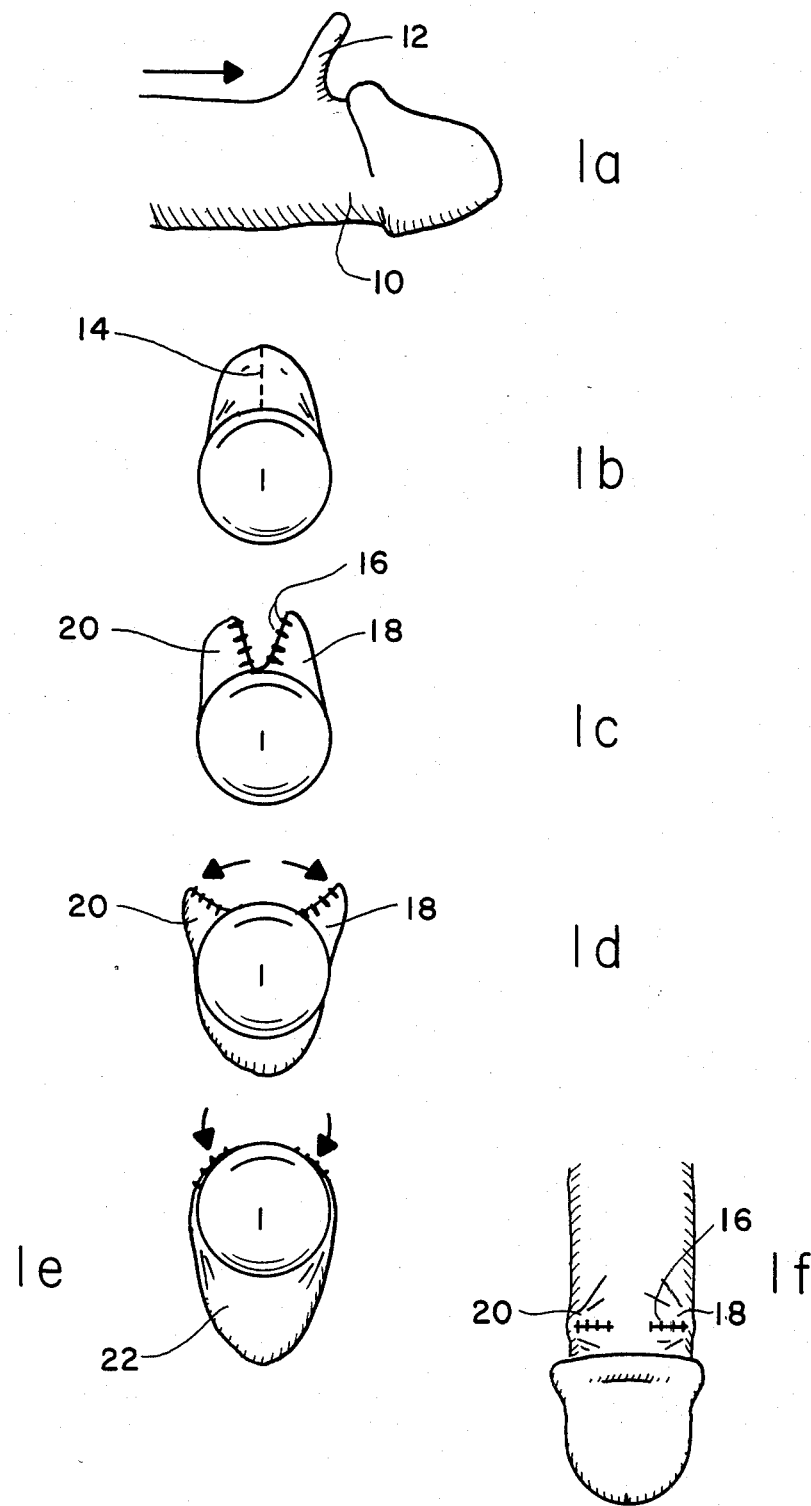
FIGS. 1(a–f) through 2(a–e) are a series of drawings illustrating the surgical procedure for circumcised males of the present invention.

FIGS. 1(a–f) through 2(a–e) shows the surgical procedure of the present invention for circumcised males.

For circumcised patients, FIG. 1a shows that all available loose skin on the top of penis 10 is pulled forward into a nap 12, just behind the glans deferens. This nap is slit, along line 14 in FIG. 1-d, cutting both layers of skin, and stitched as shown in FIG. 1-c, with stitches 16.

This procedure results in the separation of two flaps of skin, 18 and 20, shown in FIG. 1-c. Flaps 18 and 20 can be laid down, as shown in FIGS. 1-d and 1-e, to produce extra slack skin 22, on the bottom of penis 10. The top of penis 10 now looks as shown in FIG. 1-f.

Figure 2:
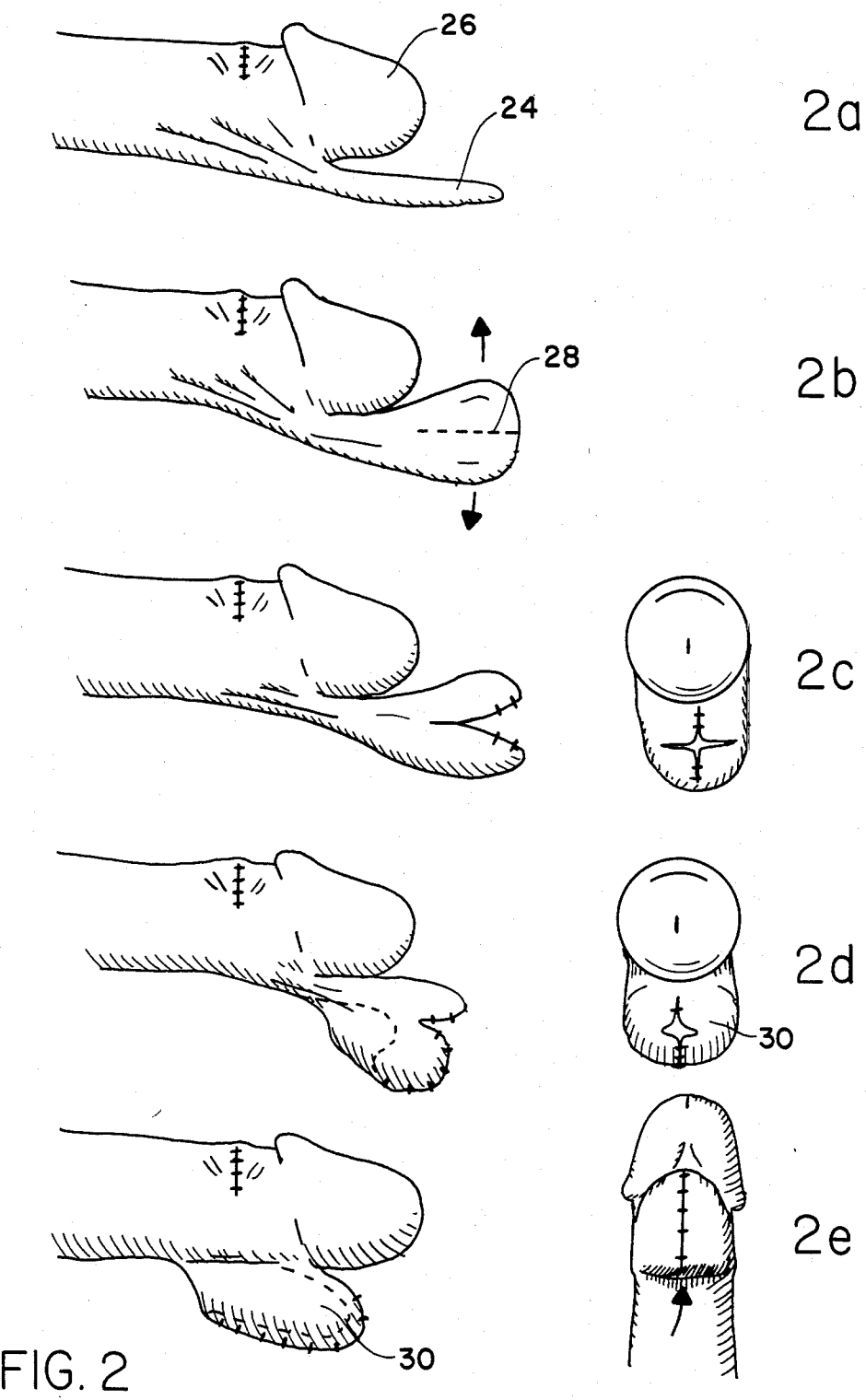

Extra loose skin 24, on the bottom of penis 10 can now be pulled forward as shown in FIG. 2-a. Skin 24 will generally extend somewhat beyond the head 26 of penis 10. This new nap of skin 24 is now stretched vertically, as shown in FIG. 2-b and slit along line 28, horizontally. Deepening this cut and stretching the skin, as the cut is made, as shown in FIGS. 2-c, 2-d, 2-e and 2-f, results in the formation of a pocket of skin, 30, capable of receiving the head of the prosthetic device taught by the present invention.

Figure 3:
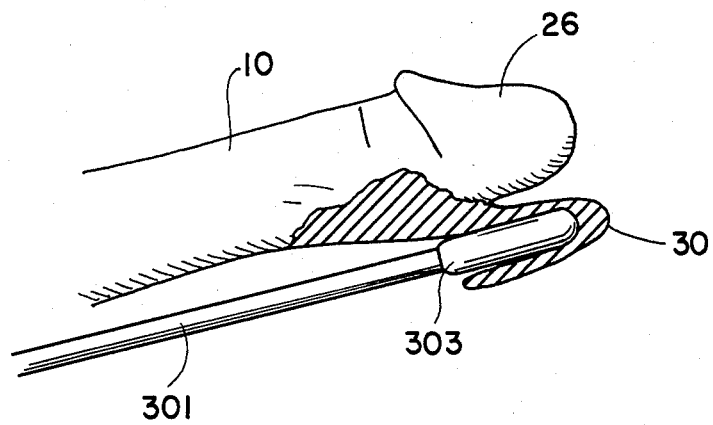
FIG. 3 illustrates a partially cut-away side view showing the engaging head of the present invention.

FIG. 3 shows an example (not necessarily exact for each person, in relation to the amount of protrusion from the head of the penis) of the cooperative engagement of the apparatus of the present invention with the surgical procedure of the present invention. In FIG. 3, penis 10 having head 26 and forward skin pocket 30, created as described above, engagingly receives head 303 of the prosthesis, which may be removably attached to shaft 301.

The surgical procedure for uncircumcised patients is much simpler, and is as follows. The foreskin is stitched closed to form a closed pocket which extends beyond the head of the penis. A slit is made in the lower side of this skin pocket, through which the head of the prosthesis can be inserted. Another larger slit is made in the pocket on its upper side, large enough for the natural head of the penis to extend therethrough. This permits the pocket to lay under the penis when not in use.

It will be noted that, in both of these procedures, the resulting surgery allows the prosthesis to be applied and removed, at the will of the patient.

Figure 4:
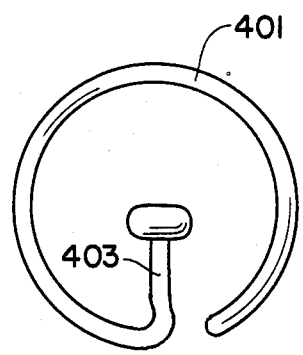
FIGS. 4-a and 4-b show two views of the apparatus taught by the present invention.
Figure 4:
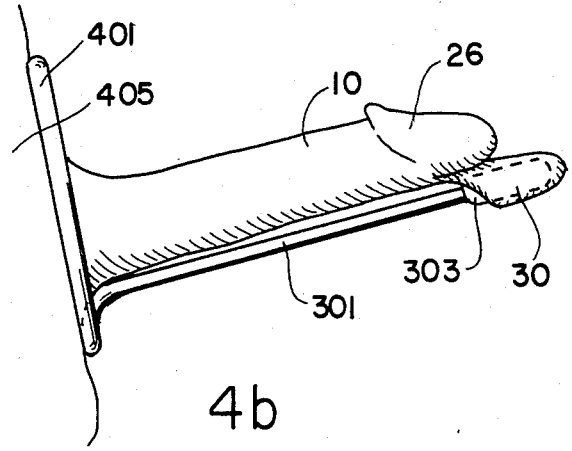

FIG. 4-a shows a front view of the apparatus of the prosthesis taught by the present invention. A padded loop 401 is shaped so as to conform to the pubic region of the patient. Loop 401 has an extension 403, which is shaft 301, shown in FIG. 3, and may be a permanent part of said loop or may be removeable. Further, it may engage the loop either fixedly or rotatably.

FIG. 4-b is a side partially cut-away view of the apparatus of the present invention, illustrating padded loop 401 in conformation with public bone 405. Shaft 403 runs up the bottom side of penis 10 and terminates shaft 301 which is engagingly received by pocket 30 near head 26 of penis 10.

Although the inventor has attempted to show the best embodiment known to him of the procedure and apparatus of the present invention, the invention is not limited to these embodiments, but should be limited only by the appended claims and their equivalents.

I claim:

1. A plastic surgery procedure for adapting a human penis to an erectile prosthesis comprising the step of:

gathering all available loose skin of a circumcised patient on the top of the penis by pulling it forward into a nap just behind the glans deferens, slitting the nap longitudinally along the length of the penis by cutting both layers of skin, stitching the cut layers of skin so as to form two flaps of skin, laying down said flaps of skin, to produce extra slack skin on the bottom of the penis, pulling forward the extra loose skin created at the bottom of the penis, somewhat beyond the head of the penis, stretching this new extra loose skin, so it is stretched vertically, slitting the new nap of skin horizontally, stitching the slit skin to form a pocket capable of receiving the head of the prosthetic device.

2. A surgical procedure for adapting the human penis to an erectile prosthesis, comprising:

stitching the foreskin of an uncircumcised patient closed, so as to form a closed pocket, which extends well beyond the head of the penis, slitting the lower side of said closed pocket so as to permit the pocket to receive the head of an erectile prosthesis, slitting the upper side of said pocket to form a large enough opening to allow the natural head of the penis to extend there through.

3. An erectile prosthesis comprising:

a padded base capable of encircling the penis and conforming in shape to the pubic region of a patient;

a rigid shaft nonrotatably engaging said base at one end, said shaft being mounted on said base so the shaft runs along the lower outer side of a patient's penis when the base is in contact with the pubic region of the patient; said shaft nonrotatably engages said base; and a smooth, rounded, elastomeric head means of greater diameter than said shaft nonrotatably affixed to said shaft at the end of said shaft opposite said base, said elastomeric head means being concentric with said shaft and of a size to fit within a compatible surgically produced pocket near the head of said penis;

the length of said shaft is such that said base is held in compression against the pubic region of the patient when the head means of said shaft engages said surgically produced skin pocket near the head of said penis.

* * * * *